(12) United States Patent
Fey (10) Patent No.: US 9,574,166 B2
(45) Date of Patent: Feb. 21, 2017

(54) BIOREACTOR SYSTEM

(75) Inventor: Stephen John Fey, Blommenslyst (DK)

(73) Assignee: DRUGMODE APS, Odense M (DK)

( * ) Notice: Subject to any disclaimer, the term of this patent is extended or adjusted under 35 U.S.C. 154(b) by 0 days.

(21) Appl. No.: 13/816,997

(22) PCT Filed: Jul. 29, 2011

(86) PCT No.: PCT/DK2011/050294
§ 371 (c)(1),
(2), (4) Date: Mar. 27, 2013

(87) PCT Pub. No.: WO2012/022351
PCT Pub. Date: Feb. 23, 2012

(65) Prior Publication Data
US 2013/0295660 A1    Nov. 7, 2013

Related U.S. Application Data

(60) Provisional application No. 61/374,637, filed on Aug. 18, 2010.

(30) Foreign Application Priority Data

Aug. 18, 2010 (DK) ................. 2010 070366

(51) Int. Cl.
*C12M 3/04* (2006.01)
*C12M 1/00* (2006.01)
*C12M 1/34* (2006.01)

(52) U.S. Cl.
CPC ............ *C12M 27/10* (2013.01); *C12M 29/04* (2013.01); *C12M 41/40* (2013.01)

(58) Field of Classification Search
CPC ................. C12M 29/04; C12M 27/10
See application file for complete search history.

(56) References Cited

U.S. PATENT DOCUMENTS

| 4,142,940 A | 3/1979 | Modolell et al. |
| 4,734,372 A | 3/1988 | Rotman |
| 4,839,292 A | 6/1989 | Cremonese |
| 5,026,650 A | 6/1991 | Schwarz et al. |
| 5,153,131 A | 10/1992 | Wolf et al. |

(Continued)

FOREIGN PATENT DOCUMENTS

| JP | 2009118820 A | 6/2009 |
| JP | 2009273399 A | 11/2009 |

(Continued)

OTHER PUBLICATIONS

International Search Report from International Application No. PCT/DK2011/050294 mailed Nov. 14, 2011.

(Continued)

*Primary Examiner* — Gautam Prakash
(74) *Attorney, Agent, or Firm* — Merchant & Gould P.C.

(57) ABSTRACT

A bioreactor or culture vessel for incubation of one or more cell cultures, tissue biopsies, cell clusters, tissue-like structures, "prototissues" or similar samples is described. The bioreactor comprises an incubation chamber, a liquid reservoir and conduction means separated from each other by semipermeable membranes. Specifically, the invention provides a humidity chamber design which simplifies the construction of the bioreactor.

23 Claims, 2 Drawing Sheets

(56) References Cited

U.S. PATENT DOCUMENTS

| | | | |
|---|---|---|---|
| 5,437,998 | A | 8/1995 | Schwarz et al. |
| 5,507,949 | A | 4/1996 | Ho |
| 5,576,211 | A | 11/1996 | Falkenberg et al. |
| 5,665,594 | A | 9/1997 | Schwarz et al. |
| 5,702,945 | A | 12/1997 | Nagels et al. |
| 5,935,845 | A | 8/1999 | Koontz |
| 5,989,913 | A | 11/1999 | Anderson et al. |
| 5,998,202 | A | 12/1999 | Schwarz et al. |
| 6,607,910 | B1 * | 8/2003 | Dimitrijevich et al. ... 435/297.1 |
| 6,642,019 | B1 | 11/2003 | Anderson et al. |
| 2004/0203140 | A1 | 10/2004 | Akers et al. |
| 2005/0084965 | A1 | 4/2005 | Silber et al. |
| 2005/0148068 | A1 | 7/2005 | Lacey et al. |
| 2010/0120136 | A1 | 5/2010 | Larsen et al. |

FOREIGN PATENT DOCUMENTS

| | | |
|---|---|---|
| WO | WO 95/07344 | 3/1995 |
| WO | WO 97/16536 | 5/1997 |
| WO | WO 2007/076865 | 7/2007 |
| WO | 2008/073313 A2 | 6/2008 |

OTHER PUBLICATIONS

International Search Report from International Application No. PCT/DK2011/050466, mailed Mar. 7, 2012.

* cited by examiner

BIOREACTOR SYSTEM

This application is a National Stage Application of PCT/DK2011/050294, filed 29 Jul. 2011, which claims benefit of Serial No. PA 2010 70366, filed 18 Aug. 2010 in Denmark, and which claims benefit of Ser. No. 61/374,637 and which applications are incorporated herein by reference. To the extent appropriate, a claim of priority is made to each of the above disclosed applications.

FIELD OF THE INVENTION

The present invention relates to a bioreactor or a culture vessel for incubation of one or more cell cultures, tissue biopsies, cell clusters, tissue-like structures, "prototissues" or similar samples. Specifically the invention provides a novel humidity chamber design which simplifies the construction of the bioreactor.

BACKGROUND OF THE INVENTION

During "classical" cell culture in an essentially flat culture vessel, cells in general and biopsies in particular tend to de-differentiate. Visibly, biopsies exhibit the 'melting ice-cream effect' as cells migrate from a block of tissue out onto the flat supporting surface of the culture vessel. Gene expression is altered in these "migrating" cells, which begin to behave biochemically as isolated cells rather than as cellular components of a differentiated tissue. De-differentiated cells express different biochemical pathways than those normally expressed by corresponding cells in an intact organism.

In contrast with "classical" cell culture conditions, "microgravity" conditions preserve the differentiation state of many types of cells in culture. Microgravity bioreactors maintain microgravity conditions by continuous rotation of a typically cylindrical or tubular incubation compartment. This rotation continuously forces cells towards the center of the incubation chamber, suspending the cells in a fluid environment using a minimum shear force. This induces them to interact and to aggregate into colonies. For microgravity culturing, cells are often initially sown out onto small (ca. 100 µm diameter) beads (this accelerates the formation of microtissue structures but is not essential). As prototissues are formed by cell growth around these beads, the beads are often ejected or become completely covered with cells. Prototissues formed in this manner become very highly differentiated so as to resemble adult tissue.

Microgravity bioreactors have been used in a variety of contexts. Early studies showed that microgravity bioreactor systems helped cells form three dimensional structures by reducing shear stress on the cells [Reduced shear stress: a major component in the ability of mammalian tissues to form three-dimensional assemblies in simulated microgravity. Goodwin T J, Prewett T L, Wolf D A, Spaulding G F. J Cell Biochem. 1993 March; 51(3):301-11.

Now a significant body of literature demonstrates increased differentiation of cells grown in a microgravity bioreactor system. For a review see: [Growing tissues in microgravity. Unsworth B R, Lelkes P I. Nat Med. 1998 August; 4(8):901-7.] For example, microgravity culturing induces neural precursor cells to form cellular clusters or "neurospheres". These prototissues are characterized by a crude, but organized, architecture, having a surface layer of immature proliferating cells (nesting-and proliferating cell nuclear antigen-positive) that enclose strata of more differentiated cells (beta-tubulin III-and glial fibrillary acidic protein-positive). These "neurospheres" show promise for development of neurotransplantable tissue. See e.g. [Neural precursor cells form rudimentary tissue-like structures in a rotating-wall vessel bioreactor. Low H P, Savarese T M, Schwartz W J. In vitro Cell Dev Biol Anim. 2001 March; 37(3):141-7.] and see [Rapid differentiation of NT2 cells in Sertoli-NT2 cell tissue constructs grown in the rotating wall bioreactor. Saporta S, Willing A E, Shamekh R, Bickford P, Paredes D, Cameron D F. Brain Res Bull. 2004 December 150; 64(4):347-56].

Or for another example, microgravity culturing of a multipotential human retinal cell line induced expression of a nearly in vivo phenotype, which could not be achieved when the cells were grown under other conditions [Generation of 3D retina-like structures from a human retinal cell line in a NASA bioreactor. Dutt K, Harris-Hooker S, Ellerson D, Layne D, Kumar R, Hunt R. Cell Transplant. 2003; 12(7):717-31.]

Some technical problems with microgravity bioreactors have been reported. For example, when temporomandibular joint (TMJ) disc tissues were engineered using either flat culture or a microgravity bioreactor, there were no significant differences in total matrix content and compressive stiffness, notwithstanding marked differences in gross appearance, histological structure, and distribution of collagen types I and II (with the bioreactor discs having more collagen type II). The authors concluded that improvements of the microgravity bioreactor culture system were needed [Detamore M S, Athanasiou K A. Use of a rotating bioreactor toward tissue engineering the temporomandibular joint disc [Tissue Eng. 2005 July-August; 11(7-8):1188-97].

A significant limitation of microgravity bioreactors of the prior art is moisture loss, which affects cell growth. De-hydration (even only by 5-10%) during incubation can result in changes in pH and other concentration-dependent parameters, such as concentrations of salts, nutrient substances, and the like. Many cell types are highly sensitive to their environment. For such cells, even a small change in such environmental conditions can influence cell growth and gene expression. This problem is especially pronounced in a small volume bioreactor, where small changes in volume can cause relatively large changes in concentration-dependent parameters. Without some solution to this de-hydration problem, a small volume bioreactor would experience rapid loss of moisture, notwithstanding maintenance of humidified conditions (100% relative humidity) in the incubator where the bioreactor was used. This tendency for rapid de-hydration in a small volume bioreactor, that is, this tendency for rapid change in relative volume greatly increases the need for time-consuming manual monitoring and manipulation, for example to replenish or exchange culture medium. This tendency effectively renders long-term maintenance of cultures in a small volume bioreactor impractical or impossible. Accordingly, it would be advantageous to provide a microgravity bioreactor with very high relative water retention in the cell incubation compartment.

WO 07/076865, WO 95/07344, U.S. Pat. Nos. 5,153,131, 5,437,998, 5,665,594, 5,989,913, and 6,642,019 each disclose improvements of microgravity bioreactors.

U.S. Pat. No. 5,576,211 describes a cell culture vessel comprising a cell culture chamber and a nutrient supply chamber separated by a membrane. Further, the cell culture vessel comprises a silicone film for exchange of oxygen and carbon dioxide in the vessel. The cell culture vessel is adapted for rotation.

However, none of these patents or published applications addresses the solution to maintaining high humidity, high gas exchange rates and low water loss from small bioreactors.

Accordingly, it is advantageous to provide an improved microgravity bioreactor that addresses this.

SUMMARY OF THE INVENTION

The invention provides a bioreactor that mitigates, alleviates eliminates or otherwise solves one or more of the above mentioned problems of the prior art.

Specifically, the present invention provides a bioreactor adapted for rotation, the bioreactor comprising
- an incubation chamber (1), the incubation chamber providing, in conjunction with a first semipermeable membrane (M1), a substantially closed confinement,
- a reservoir (3) comprising an aqueous liquid, the reservoir comprising a second semipermeable membrane (M2) arranged in fluid contact with the aqueous liquid, said membrane (M2) further being selected to promote evaporation of the aqueous liquid into a conduction means (2), and
- conduction means (2) providing a substantially enclosed conduit from the first semipermeable membrane (M1) to the second semipermeable membrane (M2), said conduction means (2) reservoir provided with ventilation means for enhancing gas exchange with the atmosphere surrounding the bioreactor,
- wherein said first semipermeable membrane (M1,) is permeable to oxygen and carbon dioxide so as to facilitate aeration of the incubation chamber (1) and the second semipermeable membrane (M2) is selected to promote evaporation of the aqueous liquid from the reservoir (3) into a conduction means (2).

In a preferred embodiment of the present invention at least said second semipermeable membrane (M2) is highly water permeable. Preferably a porous membrane is used to allow the aqueous liquid from the reservoir to enter the conduction means (2). Alternatively the second semipermeable membrane (M2) is made from a sponge-like material. In conjunction with the ventilation means the present invention provides at bioreactor ensuring that high humidity, high gas exchange rates and low water loss are maintained, which is highly challenging in small bioreactors.

In another preferred embodiment of the present invention the ventilation means is provided by actively pumping air from the atmosphere surrounding the bioreactor through an inlet opening of the conduction means, while excess air escapes the conduction means through an outlet opening.

In a particularly preferred embodiment the ventilation means is achieved by an inlet opening, i.e. formed at a cowling, in the periphery of the conduction means configured to force air from the surrounding atmosphere into the conduction means when the bioreactor rotates, while excess air escapes the conduction means through an outlet opening.

In a particularly preferred embodiment of the present invention the conduction means (2) is continuously or intermittently flushed with a $CO_2$-rich gas. In a further preferred embodiment of the present invention evaporated water from the reservoir and/or the incubation chamber provides a relative humidity in the conduction means (2) selected from the group consisting of at least 50%, at least 70%, and at least 90%. Accordingly, when being operated at 37° C. with an aqueous solution or suspension in the incubation chamber there is a relative retainment of water in the incubation chamber after 3 days of at least 95%, or a relative retainment of water in the incubation chamber after 5 days of at least 90%, or a relative retainment of water in the incubation chamber after 10 days of at least 80%.

Preferably, the incubation chamber has a substantially cylindrical shape. In such an embodiment the bioreactor is adapted for rotation around a horizontal, rotational axis by associated rotation means, said rotational axis being substantially coincident with a central axis through the incubation chamber.

The internal fluid volume of the incubation chamber is preferably selected from the group consisting of: less than 10 mL, less than 5 mL, less than 1 mL, less than 900 µL, less than 800 µL, less than 700 µL, less than 600 µL, less than 500 µL, less than 400 µL, less than 300 µL, less than 200 µL, less than 100 µL, less than 50 µL, and 25 µL.

The incubation chamber is adapted for containing one or more cell cultures, characterised in that incubation chamber is made of non-toxic materials which can be used for cell culture and which is not conducive for cell adhesion. Preferably, the incubation chamber is made of a material selected from the group consisting of various types of glass, polystyrene, polycarbonate, polypropylene, polyethylene and polymethyl methacrylate.

In a particularly preferred embodiment the incubation chamber is adapted for containing cultures of one or more types of cell cultures in the form of spheroids, on microcarrier beads or on scaffolds.

The present invention also provides a bioreactor adapted for rotation, the bioreactor comprising:
- an incubation chamber (1), the incubation chamber providing, in conjunction with a first semipermeable membrane (M1), a substantially closed confinement,
- ventilation means for establishing a flow of humidified air having a desired $CO_2$ concentration, and
- conduction means (2) providing a conduit from the first semipermeable membrane (M1) to the ventilation means,
- wherein said first semipermeable membrane (M1) is permeable to oxygen and carbon dioxide so as to facilitate aeration of the incubation chamber (1).

In this embodiment the conduction means (2) is open in the end allowing transport of a humidified gas having a desired $CO_2$ concentration; such conditioned gas may be established by enriching ambient air with $CO_2$ (e.g. from a compressed reservoir) and then humidify the air in an appropriate humidifying device. The transport of air into the conduction means (2) may be achieved with a pump 23, which can establish an appropriate flow through the conduction means (2).

Preferably the ventilation means is provided by actively pumping air from the atmosphere surrounding the bioreactor through an inlet opening 21 of the conduction means (2), while excess air escapes the conduction means (2) through an outlet opening 22. In this way the ventilation means may provide a relative humidity in the conduit selected from the group consisting of at least 50%, at least 70%, and at least 90%.

Preferred embodiments of the present invention are particularly, but not exclusively, advantageous for obtaining a microgravity bioreactor that provides:
1) Simple airtight construction.
2) Reduced consumption of resources (chemicals, cells or tissues) with corresponding reduction of cost, due to a smaller incubation compartment volume.

3) Improved moisture retention in the incubation chamber with corresponding improved maintenance of culture conditions for long-term growth, due to introduction of a reservoir.
4) Increased duration of long-term cultures incubated in a small volume bioreactor, due to improved moisture retention in the incubation chamber.
5) Reduced fluid turbulence, due to introduction of essentially zero-volume access ports.
6) Additional benefits of smaller bioreactor volume including improved monitoring of cell growth, in some embodiments by automatic video/camera imaging techniques; improved attainment of biological threshold levels of growth factors and signal molecules using smaller samples of selected biopsies or cultures; increased efficiency of standard sized incubators, due to the increased number of individual bioreactors that can be operated simultaneously.

BRIEF DESCRIPTION OF THE DRAWINGS

Some embodiments of the present invention are illustrated by the accompanying Figure, where.

DETAILED DESCRIPTION OF THE INVENTION

Definitions

As used herein, the following terms have the following meanings:

The terms "semipermeable filter" and "semipermeable membrane" refer to a filter or membrane that can be penetrated by some, but not all, chemical or biological substances. The terms are used interchangeably except that, in general, "filter" is used where water is freely permeable while, in general, "membrane" is used both where water is not freely permeable and also where water is freely permeable.

The term "incubation chamber" refers to that portion of a bioreactor in which cell cultures, tissue biopsies, cell clusters, tissue-like structures, "prototissues" or similar samples are grown, differentiated, incubated, or otherwise cultured. The term "incubation chamber" is used interchangeably with "incubation cavity" and "incubation compartment."

The term "substantially impermeable to water" is used to describe characteristics of membranes of the present invention and refers to a membrane that exhibits a high degree of repulsion of water and water-like molecules in gas and/or liquid phase.

The term "almost completely impermeable to water" is used to describe characteristics of membranes of the present invention and refers to a membrane across which the water flow rate at 1 bar is not greater than 0.1 mL/min/cm$^2$.

The term "substantially permeable to oxygen and carbon dioxide" is used to describe characteristics of membranes of the present invention and refers to a membrane across which air will readily pass.

The term "relative retainment" is used to describe conditions arising from operation of a bioreactor of the invention with an aqueous solution or suspension in the incubation chamber and refers to the relative amount of residual substance initially present. For example, the relative retainment of water in the incubation chamber (with a flexible membrane) may be calculated as the volume of the cavity after operating the bioreactor divided by the volume of the cavity at the beginning of operating the bioreactor.

The term "toxic" has the usual meaning known in the art. A "toxic" substance is a substance that in the amount present in the chemical compositions as defined above can impair the functioning of, or cause structural damage to a cell, tissue or organism.

The term "predetermined toxicity" relates to both toxic and non-toxic substances. As Paracelsus stated in the 16$^{th}$ century, "All things are poison and nothing is without poison, only the dose permits something not to be poisonous". The toxicity type of a substance may e.g. be determined according to the toxicity typing scheme of the Food and Drug Administration (FDA) of the United States of America. According to this scheme, the predetermined toxicity of a substance may belong to toxicity type A, B, etc. or may be non-toxic.

The term "cell cultures" refers to any kind of cells, tissue biopsies, cell clusters, tissue-like structures, "prototissues" or similar samples obtained or initially cultured by any method known in the art.

The term "microgravity bioreactor" refers to a bioreactor adapted for rotation.

The term "incubating under microgravity conditions" refers to growth of cell cultures in a bioreactor adapted for rotation while rotating said bioreactor about a substantially horizontal central axis at a rate that suspends one or more cell cultures in a liquid culture medium and continuing such rotation for a time period that permits growth of said one or more cell cultures.

The term "means of relative retainment of water" is used to describe features of a bioreactor and refers to any means other than perfusion that is used in combination with a membrane or filter that substantially confines the incubation chamber to achieve relative retainment of water in the incubation chamber or, in the alternative, to any single membrane that substantially confines the incubation chamber across which membrane the water flow rate at 1 bar is not greater than 0.1 mL/min/cm$^2$.

The term "chemical composition" has the usual meaning known in the art. It may include, but is not limited to, any mixture of one or more chemical or biological agents, such as small molecules, peptides, proteins, bases, nucleic acids, and lipids, wherein said chemical or biological agents result in alterations in gene expression or protein expression in one or more cell type selected from the group consisting of:

Keratinizing epithelial cells (including Epidermal keratinocyte (differentiating epidermal cell); Epidermal basal cell (stem cell); Keratinocyte of fingernails and toenails, Nail bed basal cell (stem cell); Medullary hair shaft cell; Cortical hair shaft cell; Cuticular hair shaft cell; Cuticular hair root sheath cell; Hair root sheath cell of Huxley's layer; Hair root sheath cell of Henle's layer; External hair root sheath cell; Hair matrix cell (stem cell)).

Wet stratified barrier epithelial cells (including Surface epithelial cell of stratified squamous epithelium of cornea, tongue, oral cavity, esophagus, anal canal, distal urethra and vagina; basal cell (stem cell) of epithelia of cornea, tongue, oral cavity, esophagus, anal canal, distal urethra and vagina; Urinary epithelium cell (lining urinary bladder and urinary ducts)).

Exocrine secretory epithelial cells (including Salivary gland mucous cell (polysaccharide-rich secretion); Salivary gland serous cell (glycoprotein enzyme-rich secretion); Von Ebner's gland cell in tongue (washes taste buds); Mammary gland cell (milk secretion); Lacrimal gland cell (tear secretion); Ceruminous gland cell in ear (wax secretion); Eccrine sweat gland dark cell (glycoprotein secretion); Eccrine sweat gland clear cell (small molecule secretion); Apocrine sweat gland cell (odoriferous secretion, sex-hormone sensitive); Gland of Moll cell in eyelid (specialized sweat gland); Sebaceous gland cell (lipid-rich sebum secretion); Bowman's gland cell in nose (washes olfactory epithelium); Brunner's gland cell in duodenum (enzymes and alkaline mucus); Seminal vesicle cell (secretes seminal fluid components, including fructose for swimming sperm); Prostate gland cell (secretes seminal fluid components); Bulbourethral gland cell (mucus secretion); Bartholin's gland cell (vaginal lubricant secretion); Gland of Littre cell (mucus secretion); Uterus endometrium cell (carbohydrate secretion); Isolated goblet cell of respiratory and digestive tracts (mucus secretion); Stomach lining mucous cell (mucus secretion); Gastric gland zymogenic cell (pepsinogen secretion); Gastric gland oxyntic cell (hydrochloric acid secretion); Pancreatic acinar cell (bicarbonate and digestive enzyme secretion); Paneth cell of small intestine (lysozyme secretion); Type II pneumocyte of lung (surfactant secretion); Clara cell of lung).

Hormone secreting cells (including Anterior pituitary cells; Somatotropes; Lactotropes; Thyrotropes; Gonadotropes; Corticotropes; Intermediate pituitary cell, secreting melanocyte-stimulating hormone; Magnocellular neurosecretory cells secreting oxytocin or vasopressin; Gut and respiratory tract cells (secreting one or more of the following: serotonin, endorphin, somatostatin, gastrin, secretin, cholecystokinin, insulin, glucagon, bombesin); Thyroid gland cells; thyroid epithelial cell; parafollicular cell; Parathyroid gland cells; Parathyroid chief cell; oxyphil cell; Adrenal gland cells; chromaffin cells (secreting one or more steroid hormones mineralcorticoids or glucocorticoids); Leydig cell of testes (secreting testosterone); Theca interna cell of ovarian follicle (secreting oestrogen); Corpus luteum cell of ruptured ovarian follicle (secreting progesterone); Kidney juxtaglomerular apparatus cell (secreting renin); Macula densa cell of kidney; Peripolar cell of kidney; Mesangial cell of kidney).

Epithelial absorptive cells (Gut, Exocrine Glands and Urogenital Tract) (including Intestinal brush border cell (with microvilli); Exocrine gland striated duct cell; Gall bladder epithelial cell; Kidney proximal tubule brush border cell; Kidney distal tubule cell; Ductulus efferens nonciliated cell; Epididymal principal cell; Epididymal basal cell; Metabolism and storage cells; Hepatocyte (liver cell); Adipocyte (white or brown fat cell); Liver lipocyte).

Barrier function cells (Lung, Gut, Exocrine Glands and Urogenital Tract) (including Type I pneumocyte (lining air space of lung); Pancreatic duct cell (centroacinar cell); Nonstriated duct cell (of sweat gland, salivary gland, mammary gland, etc.); Kidney glomerulus parietal cell; Kidney glomerulus podocyte; Loop of Henle thin segment cell (in kidney); Kidney collecting duct cell; Duct cell (of seminal vesicle, prostate gland, etc.)).

Epithelial cells lining closed internal body cavities (including Blood vessel and lymphatic vascular endothelial fenestrated cell; Blood vessel and lymphatic vascular endothelial continuous cell; Blood vessel and lymphatic vascular endothelial splenic cell; Synovial cell (lining joint cavities, hyaluronic acid secretion); Serosal cell (lining peritoneal, pleural, and pericardial cavities); Squamous cell (lining perilymphatic space of ear); Squamous cell (lining endolymphatic space of ear); Columnar cell of endolymphatic sac with microvilli (lining endolymphatic space of ear); Columnar cell of endolymphatic sac without microvilli (lining endolymphatic space of ear); Dark cell (lining endolymphatic space of ear); Vestibular membrane cell (lining endolymphatic space of ear); Stria vascularis basal cell (lining endolymphatic space of ear); Stria vascularis marginal cell (lining endolymphatic space of ear); Cell of Claudius (lining endolymphatic space of ear); Cell of Boettcher (lining endolymphatic space of ear); Choroid plexus cell (cerebrospinal fluid secretion); Pia-arachnoid squamous cell; Pigmented ciliary epithelium cell of eye; Nonpigmented ciliary epithelium cell of eye; Corneal endothelial cell).

Ciliated cells with propulsive function (including Respiratory tract ciliated cell; Oviduct ciliated cell (in female); Uterine endometrial ciliated cell (in female); Rete testis cilated cell (in male); Ductulus efferens ciliated cell (in male); Ciliated ependymal cell of central nervous system (lining brain cavities)).

Extracellular matrix secretion cells (including Ameloblast epithelial cell (tooth enamel secretion); Planum semilunatum epithelial cell of vestibular apparatus of ear (proteoglycan secretion); Organ of Corti interdental epithelial cell (secreting tectorial membrane covering hair cells); Loose connective tissue fibroblasts; Corneal fibroblasts; Tendon fibroblasts; Bone marrow reticular tissue fibroblasts; Other nonepithelial fibroblasts; Blood capillary pericyte; Nucleus pulposus cell of intervertebral disc; Cementoblast/cementocyte (tooth root bonelike cementum secretion); Odontoblast/odontocyte (tooth dentin secretion); Hyaline cartilage chondrocyte; Fibrocartilage chondrocyte; Elastic cartilage chondrocyte; Osteoblast/osteocyte; Osteoprogenitor cell (stem cell of osteoblasts); Hyalocyte of vitreous body of eye; Stellate cell of perilymphatic space of ear).

Contractile cells (including Red skeletal muscle cell (slow); White skeletal muscle cell (fast); Intermediate skeletal muscle cell; nuclear bag cell of Muscle spindle; nuclear chain cell of Muscle spindle; Satellite cell (stem cell); Ordinary heart muscle cell; Nodal heart muscle cell; Purkinje fiber cell; Smooth muscle cell (various types); Myoepithelial cell of iris; Myoepithelial cell of exocrine glands).

Blood and immune system cells (including Erythrocyte (red blood cell); Megakaryocyte (platelet precursor); Monocyte; Connective tissue macrophage (various types); Epidermal Langerhans cell; Osteoclast (in bone); Dendritic cell (in lymphoid tissues); Microglial cell (in central nervous system); Neutrophil granulocyte; Eosinophil granulocyte; Basophil granulocyte; Mast cell; Helper T cell; Suppressor T cell; Cytotoxic T cell; B cells; Natural killer cell; memory cell; Reticulocyte; Stem cells and committed progenitors for the blood and immune system (various types)).

Sensory transducer cells (including Photoreceptor rod cell of eye; Photoreceptor blue-sensitive cone cell of eye; Photoreceptor green-sensitive cone cell of eye; Photoreceptor red-sensitive cone cell of eye; Auditory inner hair cell of organ of Corti; Auditory outer hair cell of organ of Corti; Type I hair cell of vestibular apparatus of ear (acceleration and gravity); Type II hair cell of vestibular apparatus of ear (acceleration and gravity);

Type I taste bud cell; Olfactory receptor neuron; Basal cell of olfactory epithelium (stem cell for olfactory neurons); Type I carotid body cell (blood pH sensor); Type II carotid body cell (blood pH sensor); Merkel cell of epidermis (touch sensor); Touch-sensitive primary sensory neurons (various types); Cold-sensitive primary sensory neurons; Heat-sensitive primary sensory neurons; Pain-sensitive primary sensory neurons (various types); Proprioceptive primary sensory neurons (various types)).

Autonomic neuron cells (including Cholinergic neural cell (various types); Adrenergic neural cell (various types); Peptidergic neural cell (various types)).

Sense organ and peripheral neuron supporting cells (including Inner pillar cell of organ of Corti; Outer pillar cell of organ of Corti; Inner phalangeal cell of organ of Corti; Outer phalangeal cell of organ of Corti; Border cell of organ of Corti; Hensen cell of organ of Corti; Vestibular apparatus supporting cell; Type I taste bud supporting cell; Olfactory epithelium supporting cell; Schwann cell; Satellite cell (encapsulating peripheral nerve cell bodies); Enteric glial cell).

Central nervous system neurons and glial cells (including Neuron cells (large variety of types, still poorly classified); Astrocyte (various types); Oligodendrocyte).

Lens cells (including Anterior lens epithelial cell; Crystallin-containing lens fiber cell).

Pigment cells (including Melanocyte; Retinal pigmented epithelial cell).

Germ cells (including Oogonium/Oocyte; Spermatid; Spermatocyte; Spermatogonium cell (stem cell for spermatocyte); Spermatozoon).

Nurse cells (including Ovarian follicle cell; Sertoli cell (in testis); Thymus epithelial cell).

Stem cells (omnipotent, totipotent, pleuripotent, unipotent stem cells or precursor or progenitor cells, of both embryonic and adult origin).

All cancer cells (including teratocarcinomas of indefinable origin) derived from any of the above mentioned cell types.

Preferred Embodiments

In preferred embodiments, the semipermeable filters utilized in the present invention allow passage of molecules up to a certain molecular weight or size. Semipermeable filters with a well-defined pore size are known to the person skilled in the art and are commercially available. In preferred embodiments of the invention, semipermeable filters may be permeable to molecules up to a predetermined molecular weight, such as 50 kDa, 100kDa, 200 kDa or 250 kDa. Alternatively, the permeability of semipermeable filters may be less than or equal to 0.2 µm, even more preferably less than or equal to 0.1 µm, and most preferably less than or equal to 0.05 µm. A wide variety of filters can be used. These could be made of materials selected from (but not limited to) the group consisting of polytetrafluoroethylene (PTFE), polyvinylidene fluoride (PVDF), silicon rubber, foam plastics, radiation treated plastic, and similar materials. In one preferred embodiment, a TE 35 filter from Whatman or a ZEFLUOR filter (cat. No. 66142) from Pall Life Sciences can be used.

In preferred embodiments of the invention, the water flow rate at 1 bar across membranes that are "substantially impermeable to water" and "substantially permeable to oxygen and carbon dioxide" is not greater than 50 ml/min/$cm^2$, preferably not greater than 40 ml/min/$cm^2$, more preferably not greater than 30 ml/min/$cm^2$, even more preferably not greater than 20 ml/min/$cm^2$, most preferably not greater than 10 ml/min/$cm^2$. It will be readily understood by those skilled in the art that water permeability can be expressed in other units, which can be converted into ml/min/$cm^2$.

In preferred embodiments of the invention, the air flow rate at 3 mbar across membranes that are "substantially impermeable to water" and "substantially permeable to oxygen and carbon dioxide" is at least 5 ml/min/$cm^2$, preferably at least 10 ml/min/$cm^2$, more preferably at least 15 ml/min/$cm^2$, even more preferably at least 20 ml/min/$cm^2$, most preferably at least 25 ml/min/$cm^2$. It will be readily understood by those skilled in the art air flow can be expressed in other units, which can be converted into ml/min/$cm^2$.

Membranes comprised of a wide variety of materials can be used, that are "substantially impermeable to water" and "substantially permeable to oxygen and carbon dioxide," including but not limited to membranes well known in the art comprised of polytetrafluoroethylene (PTFE), Polyvinylidene fluoride (PVDF), silicon rubber, foam plastics, radiation treated plastic or similar materials. One example of a suitable membrane is commercially available from Whatman under the trade mark "TE 35®," a PTFE membrane with polyester support having characteristics (quoted by the manufacturer): pore size 0.2 µM, thickness 190 µM, water flow rate at 0.9 bar of 20 ml/min/$cm^2$ when measured with ethanol, air flow rate 15 ml/min/$cm^2$ at 3 mbar and bubble point 1.4 bar. Another example of a suitable membrane is commercially available from Millipore under the trade mark "SUREVENT®," a PVDF membrane having characteristics (quoted by the manufacturer): pore size 0.22 µM, thickness 100-150 µM, water breakthrough 45 mbar, air flow rate >1 slpm/$cm^2$ at 10 psi. In some embodiments, the membranes can be Millipore 0.22 µm "DURAPEL" membranes or Whatman TE 35 and TE36 membranes.

In preferred embodiments of the invention, the water flow rate at 1 bar across membranes that are "almost completely impermeable to water" while "substantially permeable to oxygen and carbon dioxide" is not greater than 0.1 ml/min/$cm^2$, even more preferably not greater than 0.05 mL/min/$cm^2$, still more preferably not greater than 0.04 ml/min/$cm^2$, even more preferably not greater than 0.03 ml/min/$cm^2$, still more preferably not greater than 0.02 ml/min/$cm^2$, most preferably not greater than 0.01 ml/min/$cm^2$. It will be readily understood by those skilled in the art that water permeability can be expressed in other units, which can be converted into ml/min/$cm^2$.

In preferred embodiments of the invention, the air flow rate at 3 mbar across membranes that are "almost completely impermeable to water" while "substantially permeable to oxygen and carbon dioxide" is at least 5 ml/min/$cm^2$, preferably at least 10 ml/min/$cm^2$, more preferably at least 15 ml/min/$cm^2$, even more preferably at least 20 ml/min/$cm^2$, most preferably at least 25 ml/min/$cm^2$.

Membranes comprised of a wide variety of materials can be used, that are "almost completely impermeable to water" while "substantially permeable to oxygen and carbon dioxide" including but not limited to membranes initially prepared for ultrafiltration purposes that have very low water permeabilities at atmospheric pressures, for example, due to low porosity and high hydrophobicity. Such membranes include ultrafiltration membranes commercially available from Amicon under the trademark "YM1®" and from Pall Corp. under the trademark "Omega 1K. ®". Other suitable membranes include thermoplastic ultrafiltration membranes prepared by thermally induced phase inversion process of semi-crystalline materials such as poly(ether ether ketone) (PEEK) and poly(phenylene sulfide)(PPS), as described by [Micro-and ultrafiltration film membranes from poly(ether ether ketone)(PEEK). Sonnenschein M, Journal of Applied Polymer Science 1999 74:1146]. Immobilized, stable supported liquid membranes (SLM) can also be used comprising a suitable oligomeric or polymeric liquid membrane material immobilized within a solid, microporous, hydrophobic support, such as the system disclosed in U.S. Pat. No. 5,507,949.

In preferred embodiments, the internal fluid volume of the incubation chamber of a bioreactor according to the present invention may be less than less than 10 mL, less than 5 mL, less than 1 mL, less than 900 µL, less than 800 µL, less than 700 µL, less than 600 µL, less than 500 µL, less than 400 µL, less than 300 µL, less than 200 µL, less than 100 µL, less than 50 µL, or 25 µL.

Many different cell cultures, tissue biopsies, cell clusters, tissue-like structures, "prototissues or similar samples may be used in practising the present invention. Different methods of cell culture include (but are not restricted to) growth in glass and plastic vessels e.g. culture flasks, cell factories or cell cubes and soft plastic bags (like infusion bags) filled with a 3D cell-supporting matrix; roller bottles; spinner bottles; fermentors; or hollow fibres of various materials. The cell cultures may be in the form of cell clusters, such as spheroids on a microcarrier bead, or cells on a scaffold (e.g. biodegradable scaffolds, often made from polyglycolic acid (PGA) PGA, polylactic acid (PLA) or a mixture of the two [Characterization of knitted polymeric scaffolds for potential use in ligament tissue engineering. Ge Z, Goh J C, Wang L, Tan E P, Lee E H. J Biomater Sci Polym Ed. 2005; 16(9):1179-92.] and [Synthesis and characterizations of biodegradable and crosslinkable poly(epsilon-caprolactone fumarate), poly(ethylene glycol fumarate), and their amphiphilic copolymer. Wang S, Lu L, Gruetzmacher J A, Currier B L, Yaszemski M J. Biomaterials. 2005 Aug. 12; [Epub ahead of print]], tissue or tissue biopsies, or tissue organoids. The invention may be practised using inter alia one or more of the following cell types:

Keratinizing epithelial cells (including Epidermal keratinocyte (differentiating epidermal cell); Epidermal basal cell (stem cell); Keratinocyte of fingernails and toenails, Nail bed basal cell (stem cell); Medullary hair shaft cell; Cortical hair shaft cell; Cuticular hair shaft cell; Cuticular hair root sheath cell; Hair root sheath cell of Huxley's layer; Hair root sheath cell of Henle's layer; External hair root sheath cell; Hair matrix cell (stem cell)).

Wet stratified barrier epithelial cells (including Surface epithelial cell of stratified squamous epithelium of cornea, tongue, oral cavity, esophagus, anal canal, distal urethra and vagina; basal cell (stem cell) of epithelia of cornea, tongue, oral cavity, esophagus, anal canal, distal urethra and vagina; Urinary epithelium cell (lining urinary bladder and urinary ducts)).

Exocrine secretory epithelial cells (including Salivary gland mucous cell (polysaccharide-rich secretion); Salivary gland serous cell (glycoprotein enzyme-rich secretion); Von Ebner's gland cell in tongue (washes taste buds); Mammary gland cell (milk secretion); Lacrimal gland cell (tear secretion); Ceruminous gland cell in ear (wax secretion); Eccrine sweat gland dark cell (glycoprotein secretion); Eccrine sweat gland clear cell (small molecule secretion); Apocrine sweat gland cell (odoriferous secretion, sex-hormone sensitive); Gland of Moll cell in eyelid (specialized sweat gland); Sebaceous gland cell (lipid-rich sebum secretion); Bowman's gland cell in nose (washes olfactory epithelium); Brunner's gland cell in duodenum (enzymes and alkaline mucus); Seminal vesicle cell (secretes seminal fluid components, including fructose for swimming sperm); Prostate gland cell (secretes seminal fluid components); Bulbourethral gland cell (mucus secretion); Bartholin's gland cell (vaginal lubricant secretion); Gland of Littre cell (mucus secretion); Uterus endometrium cell (carbohydrate secretion); Isolated goblet cell of respiratory and digestive tracts (mucus secretion); Stomach lining mucous cell (mucus secretion); Gastric gland zymogenic cell (pepsinogen secretion); Gastric gland oxyntic cell (hydrochloric acid secretion); Pancreatic acinar cell (bicarbonate and digestive enzyme secretion); Paneth cell of small intestine (lysozyme secretion); Type II pneumocyte of lung (surfactant secretion); Clara cell of lung).

Hormone secreting cells (including Anterior pituitary cells; Somatotropes; Lactotropes; Thyrotropes; Gonadotropes; Corticotropes; Intermediate pituitary cell, secreting melanocyte-stimulating hormone; Magnocellular neurosecretory cells secreting oxytocin or vasopressin; Gut and respiratory tract cells (secreting one or more of the following: serotonin, endorphin, somatostatin, gastrin, secretin, cholecystokinin, insulin, glucagon, bombesin); Thyroid gland cells; thyroid epithelial cell; parafollicular cell; Parathyroid gland cells; Parathyroid chief cell; oxyphil cell; Adrenal gland cells; chromaffin cells (secreting one or more steroid hormones mineralcorticoids or glucocorticoids); Leydig cell of testes (secreting testosterone); Theca interna cell of ovarian follicle (secreting oestrogen); Corpus luteum cell of ruptured ovarian follicle (secreting progesterone); Kidney juxtaglomerular apparatus cell (secreting renin); Macula densa cell of kidney; Peripolar cell of kidney; Mesangial cell of kidney).

Epithelial absorptive cells (Gut, Exocrine Glands and Urogenital Tract) (including Intestinal brush border cell (with microvilli); Exocrine gland striated duct cell; Gall bladder epithelial cell; Kidney proximal tubule brush border cell; Kidney distal tubule cell; Ductulus efferens nonciliated cell; Epididymal principal cell; Epididymal basal cell; Metabolism and storage cells; Hepatocyte (liver cell); Adipocyte (white or brown fat cell); Liver lipocyte).

Barrier function cells (Lung, Gut, Exocrine Glands and Urogenital Tract) (including Type I pneumocyte (lining air space of lung); Pancreatic duct cell (centroacinar cell); Nonstriated duct cell (of sweat gland, salivary gland, mammary gland, etc.); Kidney glomerulus parietal cell; Kidney glomerulus podocyte; Loop of Henle thin segment cell (in kidney); Kidney collecting duct cell; Duct cell (of seminal vesicle, prostate gland, etc.)).

Epithelial cells lining closed internal body cavities (including Blood vessel and lymphatic vascular endothelial fenestrated cell; Blood vessel and lymphatic vascular endothelial continuous cell; Blood vessel and lymphatic vascular endothelial splenic cell; Synovial cell (lining joint cavities, hyaluronic acid secretion); Serosal cell (lining peritoneal, pleural, and pericardial cavities); Squamous cell (lining perilymphatic space of ear); Squamous cell (lining endolymphatic space of ear); Columnar cell of endolymphatic sac with microvilli (lining endolymphatic space of ear); Columnar cell of endolymphatic sac without microvilli (lining endolymphatic space of ear); Dark cell (lining endolymphatic space of ear); Vestibular membrane cell (lining endolymphatic space of ear); Stria vascularis basal cell (lining endolymphatic space of ear); Stria vascularis marginal cell (lining endolymphatic space of ear); Cell of Claudius (lining endolymphatic space of ear); Cell of Boettcher (lining endolymphatic space of ear); Choroid plexus cell (cerebrospinal fluid secretion); Pia-arachnoid squamous cell; Pigmented ciliary epithelium cell of eye; Nonpigmented ciliary epithelium cell of eye; Corneal endothelial cell).

Ciliated cells with propulsive function (including Respiratory tract ciliated cell; Oviduct ciliated cell (in female); Uterine endometrial ciliated cell (in female); Rete testis ciliated cell (in male); Ductulus efferens ciliated cell (in male); Ciliated ependymal cell of central nervous system (lining brain cavities)).

Extracellular matrix secretion cells (including Ameloblast epithelial cell (tooth enamel secretion); Planum semilunatum epithelial cell of vestibular apparatus of ear (proteoglycan secretion); Organ of Corti interdental epithelial cell (secreting tectorial membrane covering hair cells); Loose connective tissue fibroblasts; Corneal fibroblasts; Tendon fibroblasts; Bone marrow reticular tissue fibroblasts; Other nonepithelial fibroblasts; Blood capillary pericyte; Nucleus pulposus cell of intervertebral disc; Cementoblast/cementocyte (tooth root bonelike cementum secretion); Odontoblast/odontocyte (tooth dentin secretion); Hyaline cartilage chondrocyte; Fibrocartilage chondrocyte; Elastic cartilage chondrocyte; Osteoblast/osteocyte; Osteoprogenitor cell (stem cell of osteoblasts); Hyalocyte of vitreous body of eye; Stellate cell of perilymphatic space of ear).

Contractile cells (including Red skeletal muscle cell (slow); White skeletal muscle cell (fast); Intermediate skeletal muscle cell; nuclear bag cell of Muscle spindle; nuclear chain cell of Muscle spindle; Satellite cell (stem cell); Ordinary heart muscle cell; Nodal heart muscle cell; Purkinje fiber cell; Smooth muscle cell (various types); Myoepithelial cell of iris; Myoepithelial cell of exocrine glands).

Blood and immune system cells (including Erythrocyte (red blood cell); Megakaryocyte (platelet precursor); Monocyte; Connective tissue macrophage (various types); Epidermal Langerhans cell; Osteoclast (in bone); Dendritic cell (in lymphoid tissues); Microglial cell (in central nervous system); Neutrophil granulocyte; Eosinophil granulocyte; Basophil granulocyte; Mast cell; Helper T cell; Suppressor T cell; Cytotoxic T cell; B cells; Natural killer cell; memory cell; Reticulocyte; Stem cells and committed progenitors for the blood and immune system (various types)).

Sensory transducer cells (including Photoreceptor rod cell of eye; Photoreceptor blue-sensitive cone cell of eye; Photoreceptor green-sensitive cone cell of eye; Photoreceptor red-sensitive cone cell of eye; Auditory inner hair cell of organ of Corti; Auditory outer hair cell of organ of Corti; Type I hair cell of vestibular apparatus of ear (acceleration and gravity); Type II hair cell of vestibular apparatus of ear (acceleration and gravity); Type I taste bud cell; Olfactory receptor neuron; Basal cell of olfactory epithelium (stem cell for olfactory neurons); Type I carotid body cell (blood pH sensor); Type II carotid body cell (blood pH sensor); Merkel cell of epidermis (touch sensor); Touch-sensitive primary sensory neurons (various types); Cold-sensitive primary sensory neurons; Heat-sensitive primary sensory neurons; Pain-sensitive primary sensory neurons (various types); Proprioceptive primary sensory neurons (various types)).

Autonomic neuron cells (including Cholinergic neural cell (various types); Adrenergic neural cell (various types); Peptidergic neural cell (various types)).

Sense organ and peripheral neuron supporting cells (including Inner pillar cell of organ of Corti; Outer pillar cell of organ of Corti; Inner phalangeal cell of organ of Corti; Outer phalangeal cell of organ of Corti; Border cell of organ of Corti; Hensen cell of organ of Corti; Vestibular apparatus supporting cell; Type I taste bud supporting cell; Olfactory epithelium supporting cell; Schwann cell; Satellite cell (encapsulating peripheral nerve cell bodies); Enteric glial cell).

Central nervous system neurons and glial cells (including Neuron cells (large variety of types, still poorly classified); Astrocyte (various types); Oligodendrocyte).

Lens cells (including Anterior lens epithelial cell; Crystallin-containing lens fiber cell).

Pigment cells (including Melanocyte; Retinal pigmented epithelial cell).

Germ cells (including Oogonium/Oocyte; Spermatid; Spermatocyte; Spermatogonium cell (stem cell for spermatocyte); Spermatozoon).

Nurse cells (including Ovarian follicle cell; Sertoli cell (in testis); Thymus epithelial cell).

Stem cells (omnipotent, totipotent, pleuripotent, unipotent stem cells or precursor or progenitor cells, of both embryonic and adult origin).

All cancer cells (including teratocarcinomas of indefinable origin) derived from any of the above mentioned cell types.

In a preferred embodiment of the invention, cells that can be applied in the context of the present invention are selected from the group consisting of hepatocytes, adipocytes, kidney cells, muscle cells, or similar cells, liver tissue, fat tissue (brown or white), liver biopsies, kidney biopsies, muscle biopsies, ovarian follicles, islets of Langerhans, and all cancer cells derived therefrom.

In a particularly preferred embodiment of the invention, cells that can be applied in the context of the present invention are hepatocytes, in particular human hepatocytes.

Figure 1:
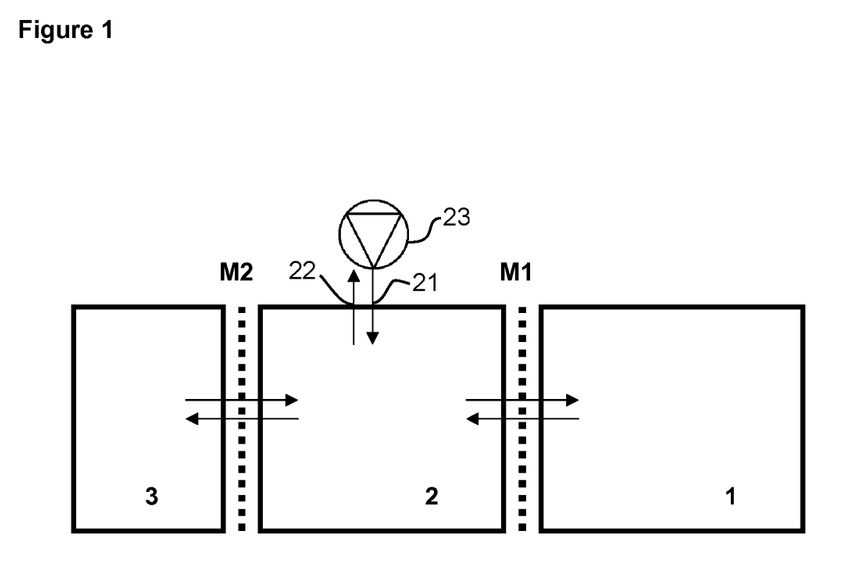
FIG. 1 is a schematic cross-sectional drawing of a bioreactor according to the present invention.

FIG. 1 is a schematic cross-sectional drawing of a bioreactor according to the present invention. The bioreactor has a high degree of rotational symmetry around a horizontal axis as viewed in FIG. 1. The reactor comprises an incubation chamber (1) for incubation of cells, tissues etc, a humidity reservoir (3), and conduction means (2) The incubation chamber (1) provides, in conjunction with a semipermeable membrane (M1) that is highly porous, a substantially closed confinement for incubation of cells etc. The pore size of the semipermeable membrane may be less than or equal to 0.5 µm, such as less than or equal to 0.3 µm, preferably less than or equal to 0.2 µm, even more preferably less than or equal to 0.1 µm, and most preferably less than or equal to 0.05 µm. Sizes less than or equal to 0.2 µm are preferable because of the need to prevent infections (e.g. bacteria, mycoplasma or yeasts) entering through the filter. In this preferred embodiment the main purpose of the semipermeable membrane is to allow exchange of atmospheric gases, such as $O_2$ and $CO_2$, while excluding cells and bacteria from entering the incubation chamber. Thus a wide variety of filters could be used for M2. These could be made of polytetrafluroethylene (PTFE), Polyvinylidene fluoride (PVDF), silicon rubber, foam plastics, radiation treated plastic or similar materials. The incubation chamber (3) has an internal fluid volume of about 25 µl to about 1 ml. Preferably, the fluid volume of the incubation chamber 15 is about 50 µl to about 0.5 ml, more preferably about 0.1 to about 0.4 ml. The small size significantly reduces the cost of use and the amount of materials (both organic and inorganic) necessary for successful operation. The small size will facilitate close-up monitoring of the cells (e.g. by remote camera), and automated processing (e.g. medium exchange in the non-perfused versions)

The humidity reservoir (3) provides a volume for an exchange of water vapour with the conduction means (2). The arrows indicate exchange of primarily gases from the surrounding atmosphere and the conduction means (2), as well as exchange of gases and vapour between the humidity reservoir, the conduction means, and the incubation chamber (1).

In the front of the bioreactor, a transparent section (not shown) may be located so that the cultivation of cells etc. may be monitored and assessed visually, either manually or automatically with e.g. a camera, from outside of the bioreactor. The transparent section could be made of glass, plastic or any other suitable materials being both transparent and biologically and chemically inert with respect to the cultivation process. Preferred materials would include (but not be limited to) various types of glass, polystyrene, polycarbonate, polypropylene, polyethylene and Polymethyl methacrylate (PMMA). Suitable variants of polymethyl methacrylate (PMMA) are available commercially including products marketed under the trademarks/trade names PERSPEX®, PLEXIGLAS®, LUCITE®, ACRYLITE®, RHOPLEX®, and OROGLAS®. Any embodiment of the bioreactor could be made in whole or in part from such transparent materials.

The incubation chamber (1) preferably has a substantially cylindrical shape but other shapes are also possible, e.g. elliptical shapes, spherical shapes etc. Preferably, the bioreactor is adapted for rotation around a horizontal, rotational axis by associated rotation means (not shown) to facilitate growth of the cells in the cavity. The rate of rotation is adjusted to maintain the cells or prototissues in suspension and this rate has to be varied as the size of the prototissues increases. The person skilled in the art will know how to adjust the rotation speed in order to maintain the cells or prototissues in suspension.

The bioreactor may be mounted on a base part by appropriate fastening means, e.g. a through going assembly screw. For easy mounting of the base part and the bioreactor on suitable rotation means (not shown), the base part may advantageously have a threaded end section. Similarly, the front part and the back part are additionally held together by an assembly screw in order to provide a fluid tight conjunction to the cavity as explained above.

In an embodiment of the invention, the conduction means (2) has an internal fluid volume of about 25 µl to about 2 ml, preferably about 50 µl to about 1 ml, most preferably about 0.1-0.4 ml. The volume of conductions means (2) should be minimal and is thereby comparable to the volume of the incubation chamber (1). The incubation chamber (1), the conduction means (2), and the reservoir (3) may be manufactured in inert plastic such as high-density poly propylene (HDPP) or similar. Preferred materials would include (but not be limited to) various types of glass, nylon, plastic, polyvinylchloride, polystyrene, polycarbonate, polypropylene, polyethylene and Polymethyl methacrylate. In combination with sealing means, e.g. O-shaped sealing rings, the air flow between the incubation chamber and the reservoir is effectively only possible through the membrane M2 (forming part of the incubation chamber) and the second membranes M1 (forming part of the reservoir).

Semipermeable membrane M1 is particular in that this membrane is less impermeable to water and substantially permeable to oxygen and carbon dioxide. Thereby the membrane M1 facilitates aeration of the incubation chamber (1). Semipermeable membrane M2 is highly permeable to water and can draw on water from the reservoir. Furthermore, there is achieved a substantial retainment of water in the incubation chamber (1) due to the impermeability for water of the membrane M1. The membrane M1 can be manufactured from a variety of materials well known in the art including but not limited to polytetrafluoroethylene (PTFE), Polyvinylidene fluoride (PVDF), silicon rubber, foam plastics, radiation treated plastic or similar materials. One example of a suitable membrane is commercially available from Whatman under the trade mark "TE 35®," a PTFE membrane with polyester support having characteristics (quoted by the manufacturer): pore size 0.2 µM, thickness 190 µM, water flow rate at 0.9 bar of 20 ml/min/cm$^2$ when measured with ethanol, air flow rate 15 ml/min/cm$^2$ at 3 mbar and bubble point 1.4 bar. Another example of a suitable membrane is commercially available from Millipore under the trade mark "SUREVENT®," a PVDF membrane having characteristics (quoted by the manufacturer): pore size 0.2 µM, thickness 100-150 µM, water breakthrough 45 mbar, air flow rate >1 slpm/cm$^2$ at 10 psi. Other examples are ZEFLUOR filters (cat. No. 66142) from Pall Life Sciences. M2 can be manufactured from any porous material allowing water vapour to permeate through the membrane. Such membranes and modified forms thereof are commercially available under the registered trademark GORE-TEX®. These expanded, porous PTFE membranes satisfy the requirements of being waterproof while also being permeable to the flow of water vapor. The expanded porous PTFE membranes are inherently hydrophobic and contain very small pores that resist the entry of liquid water even at substantial pressures or when rubbed or flexed, but readily allow the flow of water vapor. Unlike wicking materials breathability is achieved by evaporation of liquid water inside the garment or on the inner surface of the membrane followed by gaseous flow or diffusion of water vapor through the membrane to the outside.

Due to the highly hydrophobic nature of these materials water and water-like molecules will to a high degree be repelled from the surface of the membranes M1. However, some water will inevitably penetrate through the membrane M1. Evaporated water from the reservoir (1) and/or the incubation chamber (1) will provide a relative humidity of at least 50%, preferably at least 70%, or even more preferably at least 90%, such as at least 95%, 96%, 97%, 98% or 99%, in the conduit formed by the intermediate cavity (2).

Figure 2:
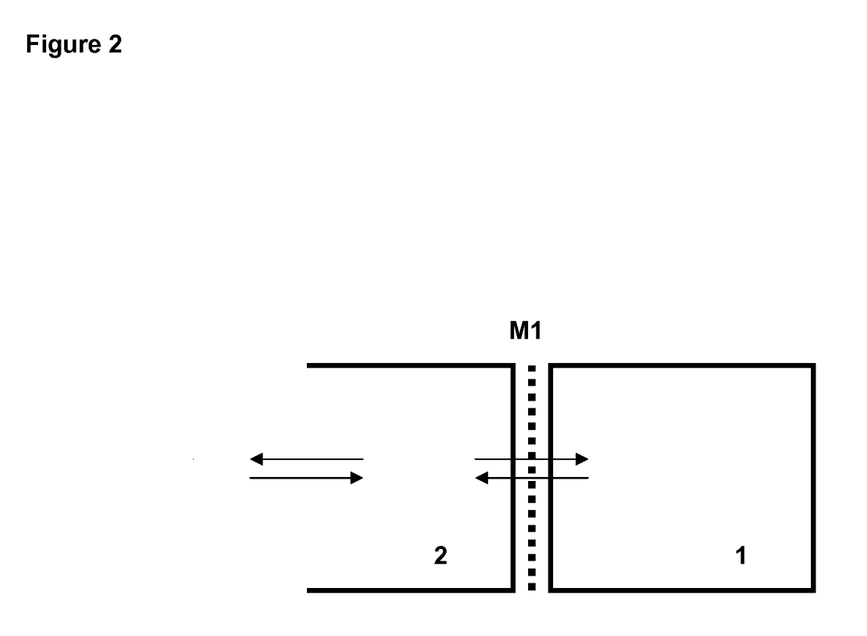
FIG. 2 is a schematic cross-sectional drawing of a bioreactor according to another embodiment of the present invention.

FIG. 2 is a schematic cross-sectional drawing of a bioreactor according to another embodiment of the present invention. In this embodiment the conduction means (2) is open in the end allowing transport of a humidified gas having a desired $CO_2$ concentration; such conditioned gas may be established by enriching ambient air with $CO_2$ (e.g. from a compressed reservoir) and then humidify the air in an appropriate humidifying device. The transport of air into the conduction means (2) may be achieved with a pump, which can establish an appropriate flow through the conduction means (2). The reactor comprises an incubation chamber (1) for incubation of cells, tissues etc, and conduction means (2) The incubation chamber (1) provides, in conjunction with a semipermeable membrane (M1) that is highly porous, a substantially closed confinement for incubation of cells etc.

The pore size of the semipermeable membrane may be less than or equal to 0.5 μm, such as less than or equal to 0.3 μm, preferably less than or equal to 0.2 μm, even more preferably less than or equal to 0.1 μm, and most preferably less than or equal to 0.05 μm. Sizes less than or equal to 0.2 μm are preferable because of the need to prevent infections (e.g. bacteria, mycoplasma or yeasts) entering through the filter. In this preferred embodiment the main purpose of the semipermeable membrane is to allow exchange of atmospheric gases, such as $O_2$ and $CO_2$, while excluding cells and bacteria from entering the incubation chamber. The incubation chamber (1) has an internal fluid volume of about 25 μl to about 1 ml. Preferably, the fluid volume of the incubation chamber 15 is about 50 μl to about 0.5 ml, more preferably about 0.1 to about 0.4 ml. The small size significantly reduces the cost of use and the amount of materials (both organic and inorganic) necessary for successful operation. The small size will facilitate close-up monitoring of the cells (e.g. by remote camera), and automated processing (e.g. medium exchange in the non-perfused versions).

The bioreactor of the present invention may be used for the incubation of one or more cell cultures, tissue biopsies, cell clusters, tissue-like structures, "prototissues" or similar samples.

A particular embodiment concerns the use of the bioreactor herein for the incubation of one or more cell cultures, wherein the one or more cell cultures are incubated for an extended period of time, such as 1 week, 2 weeks, or 3 weeks, preferably at least 1 month, such as at least 2, 3, 4, 5, 6, 7, 8, 9, 10, or 11 months, most preferably at least 12 months.

One advantage of using the bioreactor according to the present invention for the incubation of one or more cell cultures is that the cells remain in or achieve a highly differentiated state for an extended period of time. The use of the bioreactor according to the present invention furthermore avoids the use of trypsinisation to obtain the cells from the bioreactor.

By using the bioreactor of the invention for typing toxicity, the toxicity of a chemical composition of unknown toxicity can be determined with only a small amount of cells, growth medium and chemical composition. Hence, with the method of typing toxicity according to the present invention, it is possible to type the toxicity of a chemical composition with the reliability achieved when using adult human tissue, but at a much lower cost. The method according to the invention for typing toxicity may also be applied in instances where a toxicological profile is normally not created. For instance, a chemical composition of two or more compounds that are each individually non-toxic may turn out to be toxic when administered together (this phenomenon is known as 'drug-drug' interactions (even though there need be no chemical reaction between the two drugs).

Although the present invention has been described in connection with the specified embodiments, it is not intended to be limited to the specific form set forth herein. Rather, the scope of the present invention is limited only by the accompanying claims. In the claims, the term comprising does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

Each of the references cited herein is hereby incorporated by reference in its entirety. Especially the details about the bioreactor having a humidity chamber in WO 07/076865 are herewith incorporated.

The invention claimed is:

1. A bioreactor adapted for rotation, the bioreactor comprising:
    an incubation chamber comprising a substantially closed confinement limited by a first semipermeable membrane at one end of the incubation chamber,
    a reservoir for housing an aqueous liquid in an interior of the reservoir, the reservoir comprising a second semipermeable membrane arranged in fluid contact with the interior of the reservoir, and
    a conduction volume housing a gaseous atmosphere and extending between the first semipermeable membrane of the incubation chamber and the second semipermeable membrane of the reservoir, and comprising a ventilation means comprising a pump in fluid connection with an inlet opening and arranged to pump air from the atmosphere surrounding the bioreactor into the conduction volume, and an outlet opening permitting air to escape from the conduction volume,
    wherein said first semipermeable membrane is permeable to oxygen and carbon dioxide so as to facilitate aeration of the incubation chamber and the second semipermeable membrane is permeable to water vapor, oxygen, and carbon dioxide, and wherein the second semipermeable membrane has a permeability to water vapor that is greater than a permeability to water vapor of the first semipermeable membrane.

2. A bioreactor according to claim 1, wherein the ventilation means is provided by an inlet opening in the periphery of the conduction volume configured to force air from the surrounding atmosphere into the conduction volume when the bioreactor rotates, while excess air escapes the conduction volume through an outlet opening.

3. A bioreactor according to claim 1, wherein said second semipermeable membrane is made from a porous material establishing a humid environment in the conduction volume.

4. A bioreactor according to claim 1, wherein the ventilation means is arranged to continuously or intermittently flush the conduction volume with atmospheric air surrounding the bioreactor.

5. A bioreactor according to claim 1, wherein evaporated water from the reservoir and/or the incubation chamber provides a relative humidity in the conduction volume selected from the group consisting of at least 50%, at least 70%, and at least 90%.

6. A bioreactor according to claim 5, wherein the bioreactor is adapted for rotation around rotational axis by associated rotation means, said rotational axis being substantially coincident with a central axis through the incubation chamber.

7. A bioreactor according to claim 1, wherein the bioreactor, when being operated at 37° C. with an aqueous solution or suspension in the incubation chamber, has a relative retainment of water in the incubation chamber after 3 days of at least 95% of the initial volume.

8. A bioreactor according to claim 1, wherein the bioreactor, when being operated at 37° C. with an aqueous solution or suspension in the incubation chamber, has a relative retainment of water in the incubation chamber after 5 days of at least 90% of the initial volume.

9. A bioreactor according to claim 1, wherein the bioreactor, when being operated at 37° C. with an aqueous solution or suspension having an initial volume in the incubation chamber, has a relative retainment of water in the incubation chamber after 10 days of at least 80% of the initial volume.

10. A bioreactor according to claim 9, wherein the incubation chamber is made of a material selected from the group consisting of various types of glass, polystyrene, polycarbonate, polypropylene, polyethylene and polymethyl methacrylate.

11. A bioreactor according to claim 1, wherein the incubation chamber has a substantially cylindrical shape.

12. A bioreactor according to claim 1, wherein the incubation chamber has an internal fluid volume selected from the group consisting of:

less than 10 mL, less than 5 mL, less than 1 mL, less than 900 µL, less than 800 µL, less than 700 µL, less than 600 µL, less than 500 µL, less than 400 µL, less than 300 µL, less than 200 µL, less than 100 µL, less than 50 µL, and 25 µL.

13. A bioreactor according to claim 1, wherein the incubation chamber is adapted for containing one or more cell cultures, wherein the incubation chamber is made of non-toxic materials which can be used for cell culture and which is not conducive for cell adhesion.

14. A bioreactor according to claim 1, wherein the incubation chamber is adapted for containing cultures of one or more types of cell cultures either unsupported in the form of spheroids or supported in the form of microcarrier beads or scaffolds.

15. The bioreactor of claim 1, wherein the first semipermeable membrane has a water permeability rate of less than 10 mL/min/cm$^2$ at 1 bar.

16. The bioreactor of claim 1, wherein the first semipermeable membrane has a water permeability rate of less than 0.1 mL/min/cm$^2$ at 1 bar.

17. The bioreactor of claim 1, wherein the first semipermeable membrane comprises an ultrafiltration membrane.

18. The bioreactor of claim 1, wherein the incubation chamber has an internal volume of from 100 µL to 1 mL.

19. The bioreactor of claim 1, wherein the incubation chamber, conduction volume, and reservoir are arranged along a rotational axis of the bioreactor, and wherein the inlet and outlet are positioned at an outer perimeter of the conduction volume.

20. A method of incubating a cell culture in the bioreactor of claim 1, the method comprising:
supplying a cell culture and growth medium to the incubation chamber;
filling the reservoir with growth medium;
rotating the incubation chamber; and
pumping atmospheric air into the conduction volume to flush the conduction volume with the atmospheric air.

21. The method of claim 19, wherein the cell culture is incubated for at least 1 month.

22. The method of claim 19, wherein the cell culture is incubated for at least 12 months.

23. The method of claim 19, wherein the cell culture comprises hepatocytes, adipocytes, kidney cells, muscle cells, liver tissue, fat tissue, liver biopsy, kidney biopsy, muscle biopsy, ovarian follicles, islets of Langerhans, or cancer cells.

* * * * *